US00PP23632P2

(12) United States Plant Patent
Warren

(10) Patent No.: US PP23,632 P2
(45) Date of Patent: May 28, 2013

(54) SWAMP WHITE OAK TREE NAMED 'JFS-KW12'

(50) Latin Name: *Quercus bicolor*
Varietal Denomination: JFS-KW12

(75) Inventor: Keith S. Warren, Gresham, OR (US)

(73) Assignee: J. Frank Schmidt & Son Co., Boring, OR (US)

( * ) Notice: Subject to any disclaimer, the term of this patent is extended or adjusted under 35 U.S.C. 154(b) by 0 days.

(21) Appl. No.: 13/374,222

(22) Filed: Dec. 15, 2011

(51) Int. Cl.
*A01H 5/00* (2006.01)

(52) U.S. Cl.
USPC ..... Plt./225

(58) Field of Classification Search ..... Plt./225
See application file for complete search history.

*Primary Examiner* — June Hwu
*Assistant Examiner* — Louanne Krawczewicz Myers
(74) *Attorney, Agent, or Firm* — Klarquist Sparkman, LLP

(57) ABSTRACT

A variety of swamp white oak which combines vigorous growth, large deep green glossy leaves, resistance to powdery mildew and oak anthracnose, and an excellent branch structure that forms a pyramidal canopy.

10 Drawing Sheets

Latin name of the genus and species: *Quercus bicolor.*
Variety denomination: 'JFS-KW12'.

BACKGROUND

In 1998, I began a systematic program of selecting and evaluating improved seedlings of swamp white oak, *Quercus bicolor*. Between 1998 and 2005, I walked the cultivated nursery production rows of two year old trees of *Quercus bicolor* in a nursery in Boring, Oreg. During this time, I walked dozens of rows and examined over 10,000 trees. From these, 66 trees with superior features were identified, selected, and transplanted for further study. These plants were all selected from trees that originated from seed of unknown, unpatented *Quercus bicolor* trees. Of these 66 trees, 18 were chosen as finalists, assigned identifying numbers, and planted out into an evaluation block. I began propagating these 18 selected trees by chip budding into small plots on *Quercus bicolor* rootstock.

This particular invention, 'JFS-KW12' was first identified in the late summer of 2002. My attention was first drawn to it by its vigorous growth habit, its large deep green glossy leaves, and its excellent branch structure. Further observation showed that it possessed much greater resistance to powdery mildew and oak anthracnose than typical seedlings of *Quercus bicolor*. In January of 2003, I transplanted this original 'JFS-KW12' tree to a special evaluation row. In August of 2004, I began propagation of this new tree by chip budding to compare it to seedlings and to other promising selections of the species that I had identified. The transplanted row, and the propagation by chip budding, were both in a nursery in Boring, Oreg. Five trees of the 'JFS-KW12' variety were successfully propagated, were evaluated for two years, then destroyed. In each year from 2005 to 2009, I again propagated small plots of 'JFS-KW12' trees, varying from 7 to 19 trees, for testing and evaluation purposes. In each case, these trees were regularly evaluated, and after two years the trees were dug and destroyed. In 2010 and 2011, I kept a total of 30 'JFS-KW12' trees for evaluation, which were planted out under my direction and control in nursery stock blocks in Boring, Oreg. and Canby, Oreg.

From the above propagation, I established that my new variety's characteristics of vigorous growth, large deep green glossy leaves, resistance to powdery mildew and oak anthracnose, and an excellent branch structure are unique and firmly fixed in each successive generation.

SUMMARY

This new cultivar possesses a unique combination of characteristics in that it combines vigorous growth, large deep green glossy leaves, resistance to powdery mildew and oak anthracnose, and an excellent branch structure that forms a pyramidal canopy.

BRIEF DESCRIPTION OF THE DRAWINGS

The colors of an illustration of this type may vary with lighting conditions and, therefore, color characteristics of this new variety should be determined with reference to the observations described herein, rather than from these illustrations alone.

DETAILED BOTANICAL DESCRIPTION

Figure 1:
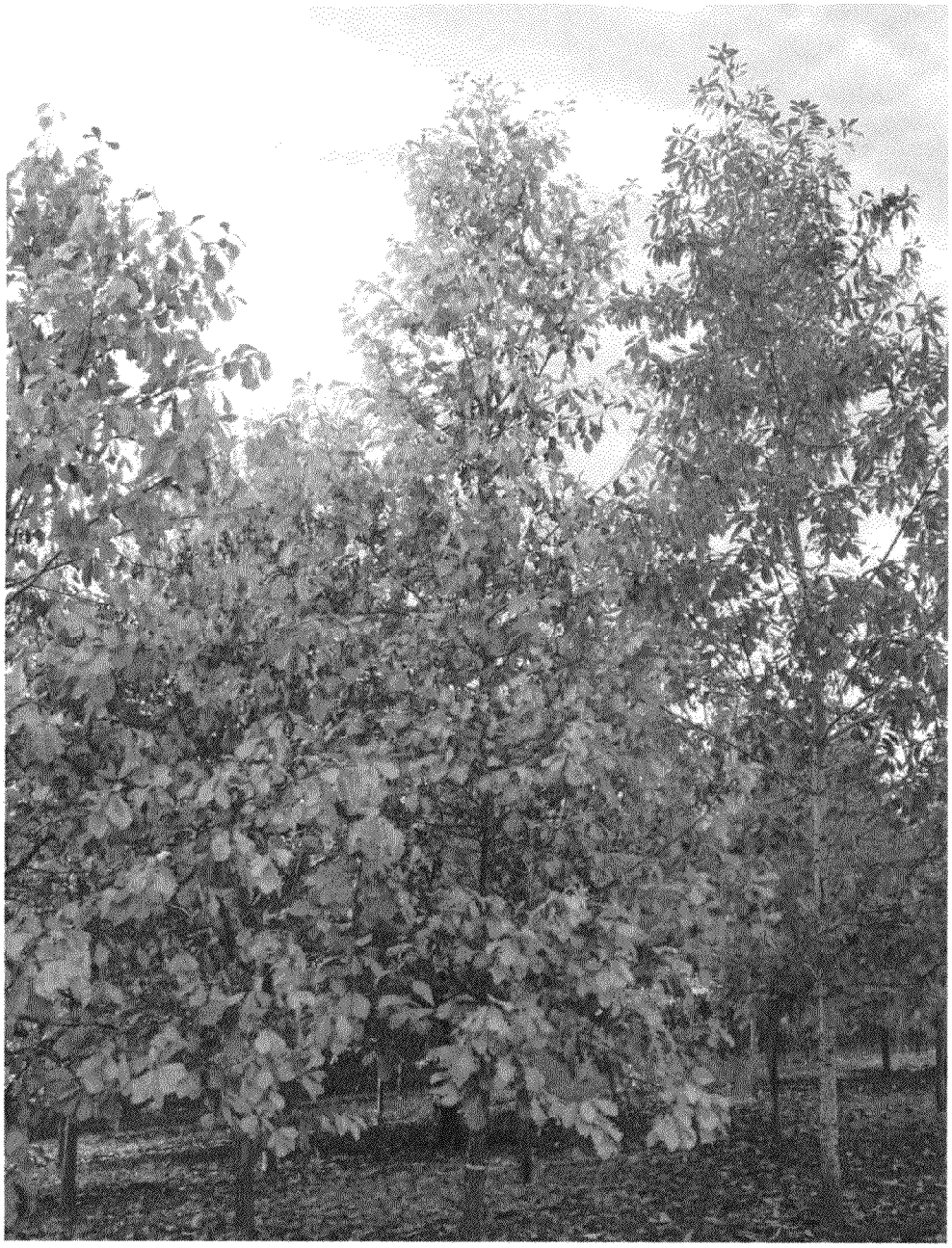
FIG. 1: Shows the original tree in the center of the photo at 11 years of age in fall color showing the straight trunk and leader, pyramidal form, and fall color.
Figure 2:
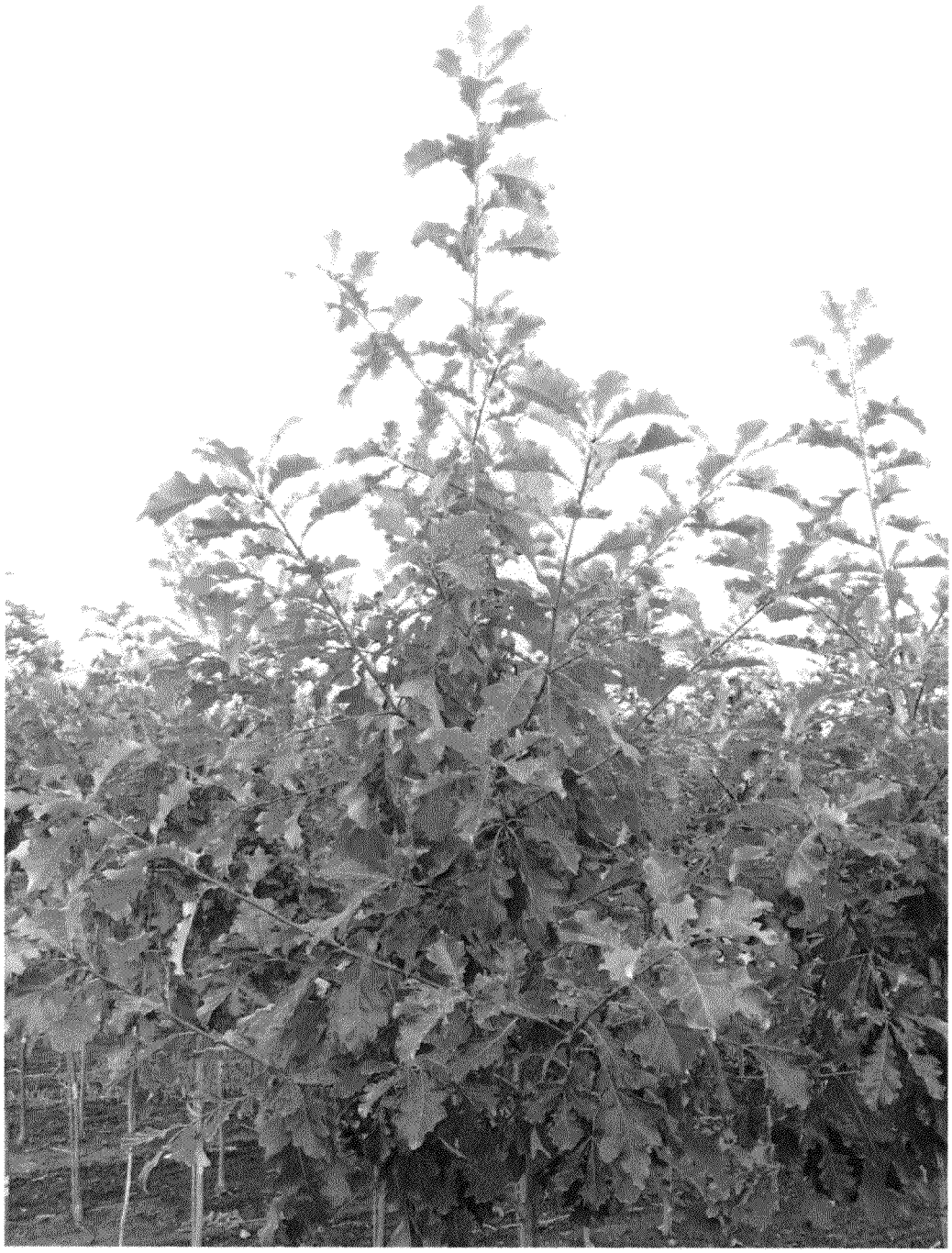
FIG. 2: Shows a two year old propagated tree illustrating pyramidal form, straight leader, and branch angles.
Figure 3:
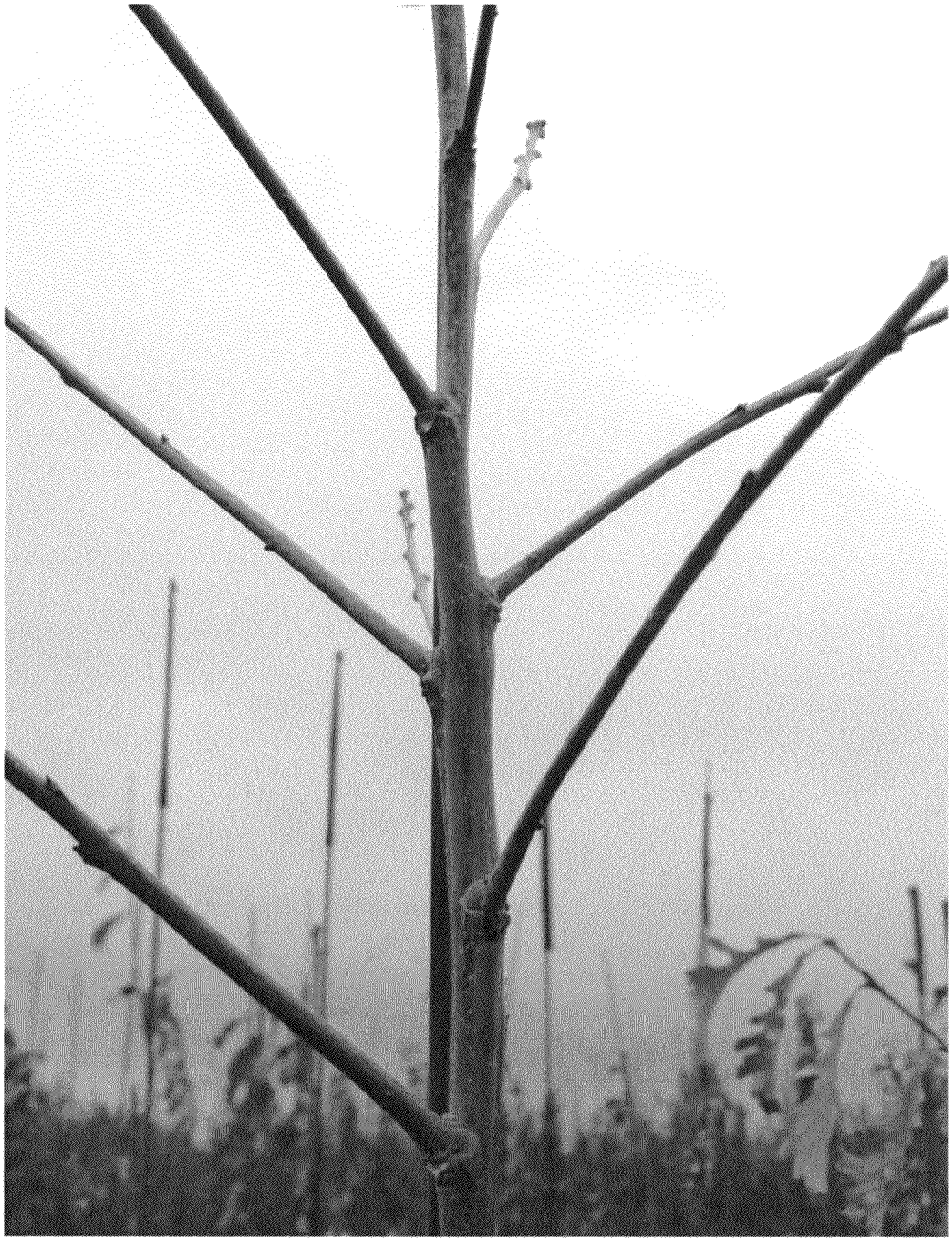
FIG. 3: Shows a portion of a one year old tree with strong branching and typical uniform branch angles.
Figure 4:
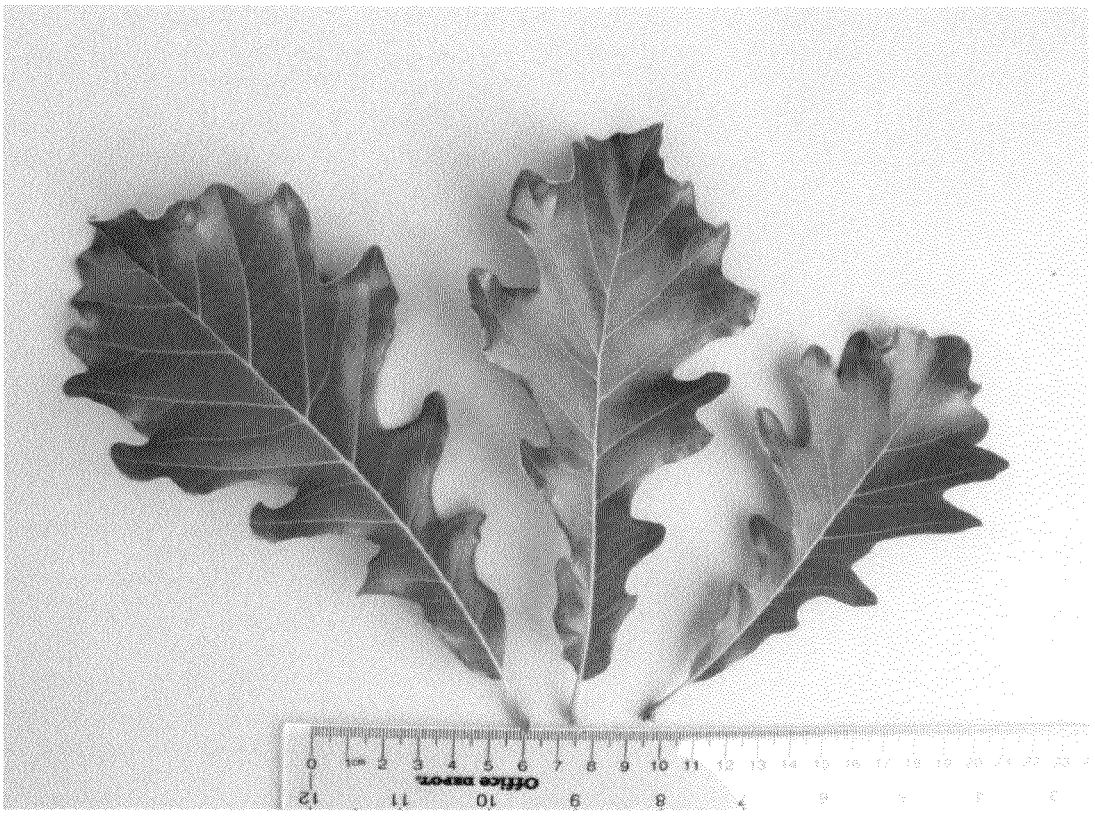
FIG. 4: Shows the upper surface of foliage in summer color.
Figure 5:
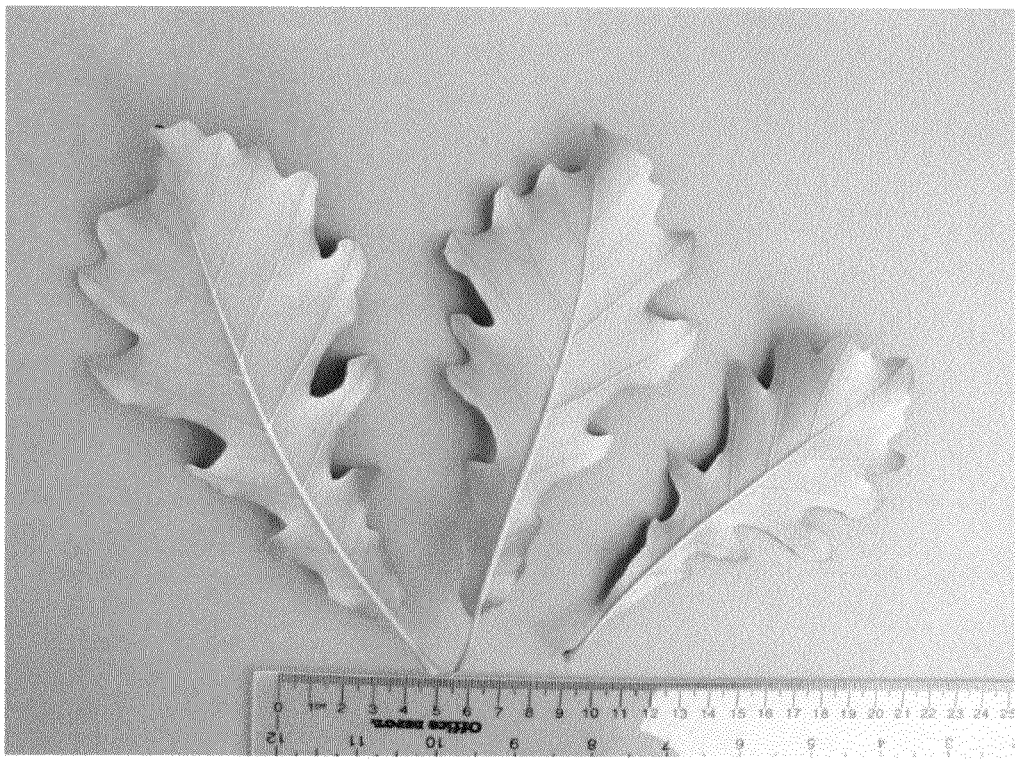
FIG. 5: Shows the lower surface of foliage in summer color.
Figure 6:
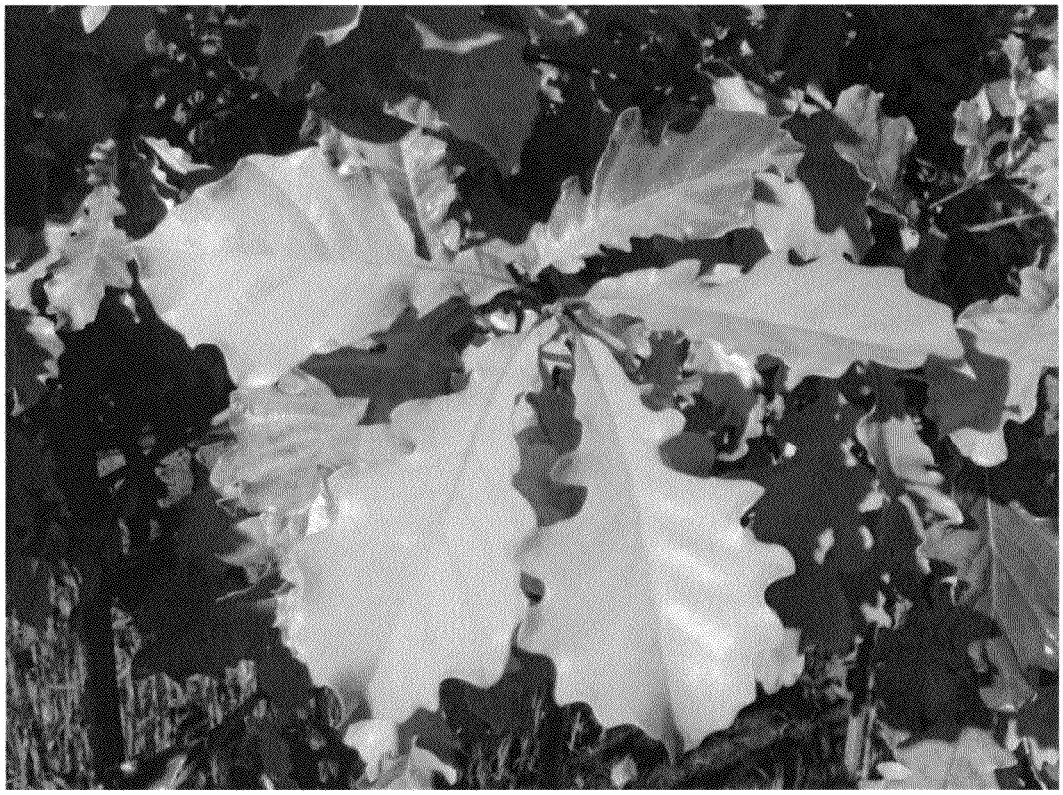
FIG. 6: Show fall color progressively developing on the foliage of a two year old tree.
Figure 7:
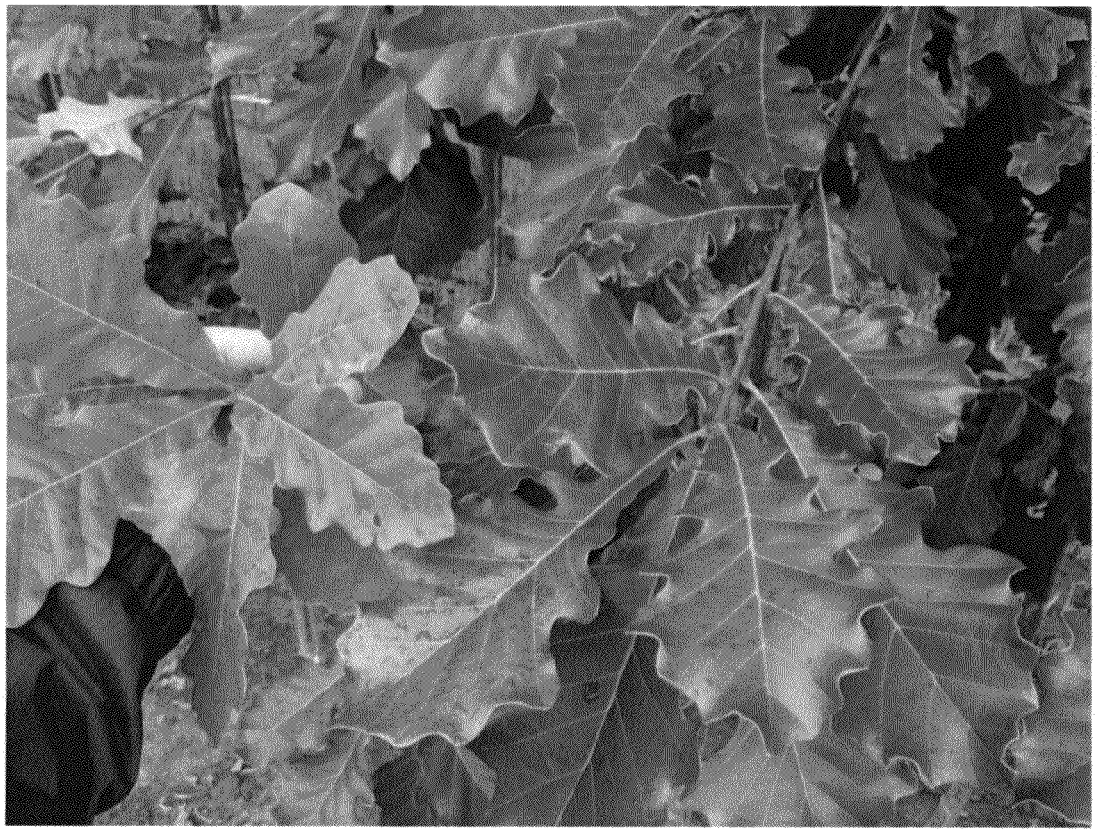
FIG. 7: Shows the large, glossy, deeply colored leaves of 'JFS-KW12' on the right and typical leaves of *Quercus bicolor* seedlings held in my hand on the left.
Figure 8:
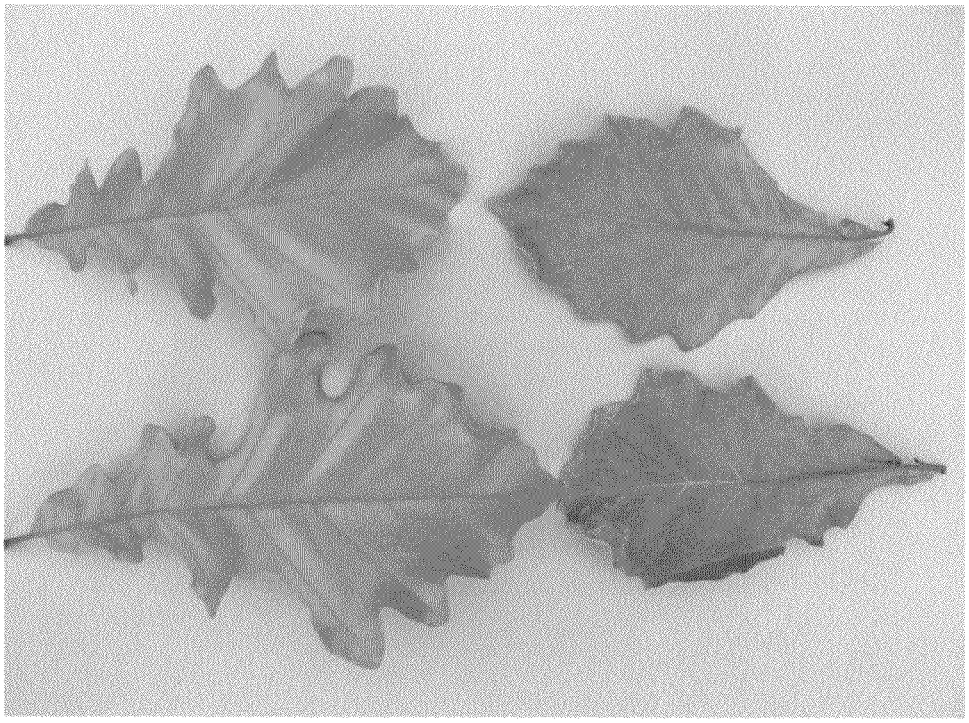
FIG. 8: Shows the upper surface of marcescent leaves in November, with 'JFS-KW12' on the left and leaves from *Quercus bicolor* seedlings on the right, and illustrating the brighter appearance of 'JFS-KW12'.
Figure 9:
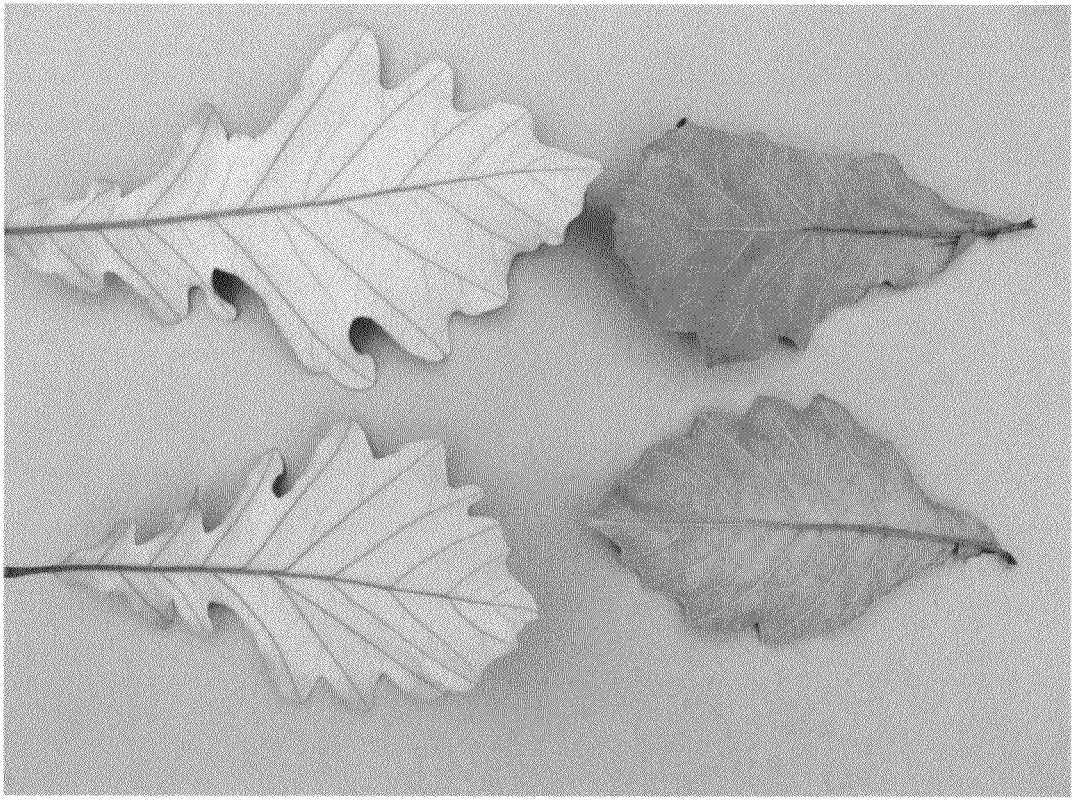
FIG. 9: Shows the lower surface of marcescent leaves in November, with 'JFS-KW12' on the left and leaves from *Quercus bicolor* seedlings on the right, and illustrating the light appearance of 'JFS-KW12'.
Figure 10:
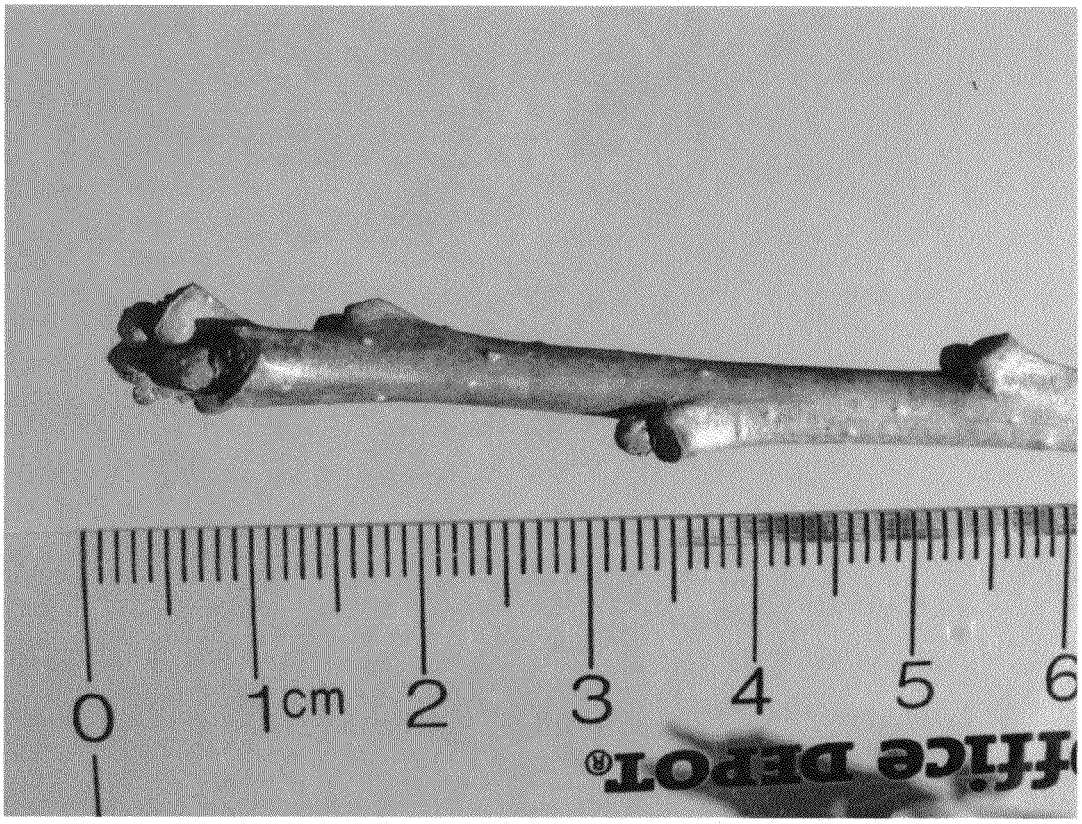
FIG. 10: Shows a dormant twig of a 2 year old propagated tree and winter buds.

The following detailed description of the 'JFS-KW12' variety, with color terminology in accordance with The Royal Horticultural Society (R.H.S.), London, Colour Chart© 1986, is based on observations of the original tree and one and two year old progeny. The observed progeny were trees that were growing in Boring, Oreg.

Scientific name: *Quercus bicolor* 'JFS-KW12'.

Parentage:

*Seed parent.*—*Quercus bicolor.*

*Pollen parent.*—*Quercus bicolor.*

Tree:

*Overall shape.*—Straight, sturdy, strong growing, upright pyramidal tree with a strong central leader and upward angled branches.

*Growth rate.*—Moderately fast; faster than typical trees of the species.

*Height.*—Original tree; 6.8 meters at 11 years of age.

*Width.*—Original tree; 2.9 meters at 11 years of age.

*Trunk diameter.*—Original tree; 13.4 cm at 10 cm from ground; 12.0 cm at 1 meter, at 11 years of age.

*Trunk.*—Original tree; sturdy, very straight.

*Trunk bark texture.*—Original tree; rough, shallowly furrowed, partially peeling in vertical strips.

*Trunk bark color.*—Immature bark color: Grey-Green 197A. Mature bark color: A combination of Grey-Brown 199B and Grey-Green 197B to 197A. The peeling bark strips are mostly Grey-Green 197E and the more firmly attached sections of the bark are mostly Grey-Brown 199B. Lenticels: None visible on the mature trunk.

*Primary branches.*—Sturdy, radiating outward and upward at a uniform angle. Branch length varies uniformly from shorter branches at the top of the tree to longer branches at the base, creating a pyramidal canopy. On propagated one year old and two year old trees, the same pyramidal shape is evidenced by shorter branches near top of the tree and longer branches below.

*Branch angle.*—Branch angle varies progressively from the top of the tree to the bottom, with angles of 45° at the top and increasing gradually to 80° at the bottom, as measured on the original tree.

*Branch lenticels.*—Oval, 1.0 mm by 0.5 mm, Orange-White 159A.

*Branch bark.*—Smooth when young. The color is Grey-Brown 199A to 199B on one year old branches which changes to Grey-Green 197A to Black 202A in the second and third year.

*Dormant buds.*—Imbricate, broadly ovate to rounded, Greyed-Orange 165A to Greyed-Orange 165B. Slightly pubescent. 2 mm to 3 mm long by about 2 mm to 3 mm in diameter, but very slightly appressed.

*Internodes.*—1.5 cm to 4.0 cm when measured on branches of two year old trees, average length 2.6 cm.

*Hardiness.*—My new variety has tolerated temperatures to 10 degrees F. without damage in Boring, Oreg. My new variety has not been tested at lower temperatures, but it is believed to have Zone 4 cold hardiness similar to the species.

*Disease resistance.*—Highly resistant to powdery mildew and to oak anthracnose when compared to typical seedlings of the species.

Leaves: Except as otherwise noted, observations are from twenty typical vigorous growth leaves.

*Arrangement.*—Alternate.

*Texture.*—Smooth on upper surface, velvety below.

*Sheen.*—Very glossy on upper surface.

*Length.*—12 cm to 24 cm when measured on two year old trees.

*Width.*—6 cm to 14 cm when measured on two year old trees.

*Petioles.*—14 mm to 24 mm long by 1.5 to 3.0 mm in diameter. Smooth textured. Yellow-Green 145B on the lower surface. Yellow-Green 145A on the upper surface with tint of Orange-Red 31A on sun exposed surfaces, especially at the base. This Orange-Red 31A color intensifies in late summer and becomes Orange Red 34A at the time the leaf blade is in fall color.

*Overall shape.*—Obovate.

*Leaf orientation.*—Variable, depending on position in the canopy, from upward angled to drooping. Leaves highest in the canopy tend to be most upward, and lower leaves tend to droop.

*Margin.*—Undulate to moderately lobed, with the deepest lobes found in the central to proximal portion of the leaf blade. The deepest sinuses typically extend about halfway to the midrib.

*Tip.*—Broadly rounded with an undulate margin.

*Base.*—Cuneate.

*Stipules.*—None.

*Veination.*—Pinnate, quite prominent on the underside.

*Spring leaf color, first emerging leaves.*—Green 143A with a tint of Greyed-Red 179A over the top.

*Summer leaf color.*—Upper leaf surface: Green 135A to Green 136B. Lower leaf surface: Green-White 157A to Greyed-Green 192B. Vein: Yellow-Green 145A to Yellow-Green 145B on the upper surface and Yellow-Green 145C on the lower surface.

*Fall leaf color.*—Fall color typically begins as Yellow-Orange 22C, then progresses to Yellow-Orange 22B and then to Yellow-Orange 22A over a period of about a week. After the foliage achieves full fall color, the leaves become more dull in color over a period of about a week and hold on the tree in a marcescent condition for a period of one to two months, gradually defoliating over this period of time. During the marcescent period, leaf color is Greyed-Orange 165B on the upper surface and Greyed-Orange 165C to Greyed-Orange 165D on the lower surface.

*Pubescence.*—Heavily pubescent on the underside with a short, thick, velvety tomentum. Glabrous on top.

*Persistence.*—Tree is partially marcescent, holding some leaves for one to two months after fall color, then becomes completely deciduous.

Flowers: The original tree and its progeny have not yet flowered.

Fruit: The original tree and its progeny have not yet set fruit.

Comparison to the species: Compared to typical seedlings of the species *Quercus bicolor*, my new variety is faster growing in both height and stem diameter, produces a greater number of branches with greater length, has larger leaves, has a more uniform branch angle, and has darker summer foliage and a brighter marcescent leaf color. In addition, my new variety has much improved resistance to powdery mildew and oak anthracnose. Measurements of one and two year old trees of my new variety and seedlings of the species show size and form differences. Evaluation of the original tree and propagated trees show the foliage quality differences. These differences are detailed in Table 1, Table 2, and Table 3 below.

TABLE 1

| 1 Year Tree Feature: | 'JFS-KW12' | *Quercus bicolor* Seedling |
|---|---|---|
| Height | 1.9 m | 1.6 m |
| Trunk diameter | 17 mm | 11 mm |
| Number of branches | 5.8 | 1.1 |
| Average length of longest branch | 55 cm | 26 cm |
| Branch angle | 40° to 50° | 60° to 90° |

TABLE 2

| 2 Year Tree Feature: | 'JFS-KW12' | *Quercus bicolor* Seedling |
|---|---|---|
| Height | 2.9 m | 2.1 m |
| Trunk diameter at 10 cm | 2.6 cm | 2.1 cm |
| Number of branches longer than 10 cm | 11.3 | 5.0 |

TABLE 2-continued

| 2 Year Tree Feature: | 'JFS-KW12' | *Quercus bicolor* Seedling |
|---|---|---|
| Average length of lower four branches | 144 cm | 92 cm |
| Average leaf length | 19 cm | 14 cm |

TABLE 3

| Foliage Feature: | 'JFS-KW12' | *Quercus bicolor* Seedling |
|---|---|---|
| Leaf color of upper surface in summer | Green 135A to Green 136B | Green 138A to Green 143A |
| Leaf color of lower surface in summer | Green-White 157A to Greyed-Green 192B | Yellow-Green 144A |
| Leaf surface sheen in summer | Very glossy | Dull to satiny |
| Marcescent leaf color of upper surface | Greyed-Orange 165B | Greyed-Orange 177A to Greyed-Orange 177B |
| Marcescent leaf color of lower surface | Greyed-Orange 165C to Greyed-Orange 165D | Greyed-Orange 177B |
| Powdery mildew susceptibility | Highly resistant | Moderately susceptible |
| Oak anthracnose susceptibility | Resistant | Very susceptible |

I claim:

1. A new and distinct variety of swamp white oak, substantially as herein shown and described.

* * * * *